(12) United States Patent
Park et al.

(10) Patent No.: US 9,831,137 B2
(45) Date of Patent: Nov. 28, 2017

(54) DEFECT IMAGING APPARATUS, DEFECT DETECTION SYSTEM HAVING THE SAME, AND METHOD OF DETECTING DEFECTS USING THE SAME

(71) Applicant: Samsung Electronics Co., Ltd., Suwon-si, Gyeonggi-do (KR)

(72) Inventors: Il-Suk Park, Hwaseong-si (KR); Hyung-Suk Cho, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/177,938

(22) Filed: Jun. 9, 2016

(65) Prior Publication Data

US 2017/0076435 A1  Mar. 16, 2017

(30) Foreign Application Priority Data

Sep. 15, 2015 (KR) .................. 10-2015-0130129

(51) Int. Cl.
G06T 7/00 (2017.01)
H01L 21/66 (2006.01)
G01N 21/95 (2006.01)

(52) U.S. Cl.
CPC ......... *H01L 22/12* (2013.01); *G01N 21/9501* (2013.01)

(58) Field of Classification Search
CPC ..... G03F 1/38; G03F 1/42; G03F 1/44; G06T 7/70; G06T 2207/30148; B23Q 17/2452; B23Q 17/2457; B23Q 17/2471; B23Q 17/249; G05B 2219/31432; G05B 2219/36251
See application file for complete search history.

(56) References Cited

U.S. PATENT DOCUMENTS

| | | | |
|---|---|---|---|
| 6,724,005 B2 | 4/2004 | Tokumoto | |
| 7,217,925 B2 | 5/2007 | Nakada et al. | |
| 7,474,394 B2 | 1/2009 | Hamamatsu et al. | |
| 2013/0162871 A1 | 6/2013 | Bosco et al. | |
| 2013/0277553 A1 | 10/2013 | Otani et al. | |

FOREIGN PATENT DOCUMENTS

| | | |
|---|---|---|
| JP | 2000-180391 A | 6/2000 |
| JP | 2003-227710 A | 8/2003 |
| JP | 2008-218259 A | 9/2008 |
| KR | 2002-0058309 A | 7/2002 |
| KR | 2006-0079479 A | 7/2006 |

*Primary Examiner* — Duy M Dang
(74) *Attorney, Agent, or Firm* — Harness, Dickey & Pierce, P.L.C.

(57) ABSTRACT

The defect imaging apparatus including a chamber having a stage to which a substrate having at least one process defect and at least one reference defects defined at a given area is secured, a position controller configured to obtain an imaging error from a detected actual position and a conversion position of the reference defect and correct a conversion position of the process defect by the imaging error, and generate an irradiation position corresponding to an actual position of the process defect, an image signal generator configured to generate an image signal of the process defect by irradiating an electron beam to the irradiation position and detecting charged particles from the irradiation position in response to the irradiated electron beam, and an imaging device configured to generate a defect image of the process defect by processing the generated image signal may be provided.

20 Claims, 8 Drawing Sheets

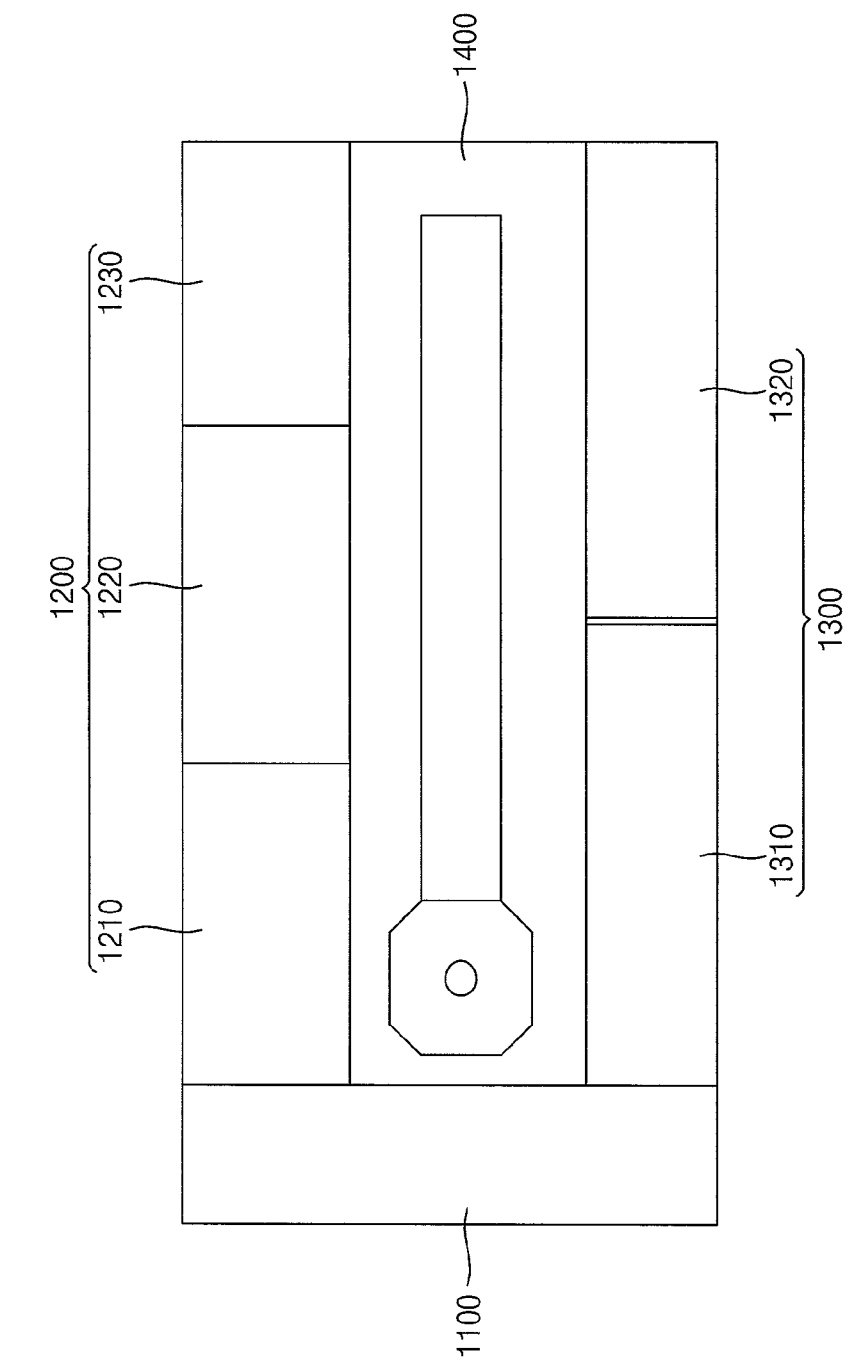

DEFECT IMAGING APPARATUS, DEFECT DETECTION SYSTEM HAVING THE SAME, AND METHOD OF DETECTING DEFECTS USING THE SAME

CROSS-REFERENCE TO RELATED APPLICATIONS

This application claims priority under 35 U.S.C §119 to Korean Patent Application No. 10-2015-0130129 filed on Sep. 15, 2015 in the Korean Intellectual Property Office, the contents of which are incorporated by reference herein in its entirety.

BACKGROUND

1. Field

Example embodiments relate to defect imaging apparatuses for imaging defects, defect detection systems having the same, and/or methods of inspecting defects using the same.

2. Description of the Related Art

Defect positions on a semiconductor substrate such as a wafer are detected by an optical inspection apparatus and defect images corresponding to the defect positions are obtained by a defect imaging apparatus. The defect image usually shows the shape and characteristics of the corresponding defect. Thus, the operator may identify defects on the wafer based on the defect image.

To obtain accurate defect images, the beam irradiator of the defect imaging apparatus needs to be aligned to the defect position detected by the optical inspection apparatus. Thus, coordinate conversion between the defect imaging apparatus and the inspection apparatus may be desired before the operation of the defect imaging apparatus together with correction of equipment errors considering operation errors and instrumental errors of the inspection apparatus and the defect imaging apparatus.

In a conventional defect imaging process, the wafer has been manually searched over and a reference defect having a sufficient size for the error correction has been selected by an operator for the coordinate conversion and the error correction. Then, the manually-detected central position of the reference defect is compared with an inspected central position of the same reference defect detected by the inspection apparatus. The imaging operator usually obtains the equipment errors just by calculating the difference between the manually-detected central position and the inspected central position of the reference defect.

However, the manual detection of the central position of the reference defect usually takes relatively long time, which results in considerable efficiency reduction of the manufacturing process for semiconductor devices. Further, recent technical trends towards a smaller size and a finer pattern in semiconductor devices make it more challenging to find a reference defect having a size appropriate for the manual search. Therefore, correction of the equipment errors and coordinate conversion between the inspection apparatus and the defect imaging apparatus take longer times.

For example, when a number of the inspection apparatuses and a number of the defect imaging apparatuses are desired for an efficiency of the defect detection, a setup time for the imaging error correction and coordinate conversion may considerably increase, thereby significantly reducing manufacturing efficiency of the semiconductor devices.

SUMMARY

Some example embodiments of the present inventive concepts provide defect imaging apparatuses for automatically detecting the imaging errors by using a reference pattern that may be provided at a desired (Or alternatively, predetermined) area of a substrate.

Some example embodiments of the present inventive concepts provide defect detection systems for detecting defects from a substrate and making defect images of the defects using the above defect imaging apparatus.

Some example embodiments of the present inventive concepts provide methods of detecting defects from a substrate including relatively fine pattern structures and making the defect image of the defects using the above defect imaging apparatus.

According to an example embodiment of the inventive concepts, a defect imaging apparatus includes a chamber having a stage to which a substrate having at least one reference and at least one process defect is secured, a position controller configured to obtain an imaging error from an detected actual position and a conversion position of the reference defect, the position controller further configured to correct a conversion position of the process defect by the imaging error and generate an irradiation position corresponding to an actual location of the process defect, an image signal generator configured to generate an image signal of the process defect by irradiating an electron beam to the irradiation position and detecting charged particles discharged from the irradiation position in response to the irradiated electron beam, and an imaging device configured to generate a defect image of the process defect by processing the generated image signal. The at least one process defect may include a plurality of the process defects, which are randomly distributed on the substrate, and the reference defect may be located at a given area on the substrate.

In an example embodiment, the position control may include a conversion unit configured to convert inspection positions of the reference defect and the process defect, which may be detected by an inspection apparatus on a basis of an inspection coordinate system, to conversion positions thereof on a basis of an imaging coordinate system, a search unit configured to search the reference defect on the substrate and detect an actual position of the reference defect on a basis of the imaging coordinate system, an error generator configured to generate a difference between the actual position and the conversion position of the reference defect as the imaging error, and a correction unit correcting configured to correct the conversion point of the process defect based on the imaging error and generate the irradiation position based on the corrected conversion point.

In an example embodiment, the reference defect may have a size of about 100 nm to about 900 nm and the search unit may be configured to search the reference defect by a unit of a square-shaped field of view having a size of about 3 µm×3 µm to about 5 µm×5 µm.

In an example embodiment, when the at least one reference defect includes a plurality of reference defects, the error generator may be configured to generate a plurality of differences between a plurality of actual positions and a plurality of conversion positions with respect to the reference defects, and the error generator may be further configured to generate a statistical equivalent imaging error (SEIE) as the imaging error, the SEIE being a value at which a mean value of deviation between each of the plurality of differences is statistically minimized.

In an example embodiment, the imaging coordinate system may include a Cartesian coordinate system and x and y components of the statistical equivalent imaging error may be determined by a regression line that may be expressed into a first order polynomial by a least square method.

In an example embodiment, the correction unit may include a first buffer, a second buffer, and a coordinate connector. The first buffer may be configured to receive the conversion positions of the process defects from the conversion unit. The second buffer may be configured to receive the imaging error from the error generator. The coordinate corrector may be configured to correct a coordinate value of the conversion position of the process defect based on the imaging error and generate the irradiation position.

In an example embodiment, the defect imaging apparatus may further include a scan controller connected to the position controller, the scan controller configured to control at least one of the image signal generator or the stage such that the electron beam a be focused to the irradiation position.

In an example embodiment, the scan controller may include an irradiator controller configured to control a beam irradiator such that a beam path of the electron beam generated by the beam irradiator may be directed to the irradiation position. A stage controller may be configured to control the stage such that the irradiation position is aligned with the beam irradiator and the electron beam generated by the beam irradiator is directed to the irradiation position.

According to an example embodiments of the inventive concepts, a defect detection system includes at least an inspection apparatus in which a substrate having a plurality of process defects and at least a reference defect may be inspected to thereby generate inspection positions of the reference defect and the process defects based on an inspection coordinate system, and at least a defect imaging apparatus into which the substrate may be transferred from the inspection apparatus The inspection positions may be converted into conversion position of the reference and process defects based on an imaging coordinate system and making a defect image of the process defect by using an imaging error that may be automatically generated from the conversion position and an actual position of the reference defect. In such a case, the defect imaging apparatus may include a position controller automatically obtaining the imaging error from the actual position that may be automatically detected and the conversion position of the reference defect and correcting the conversion position of the process defect by the imaging error to thereby generate an irradiation position at which the process defect may be located, an image signal generator generating image signals of the process defect by irradiating electron beams to the irradiation position and detecting charged particles discharged from the irradiation position in response to the electron beam, and an imaging device making the defect image of the process defect by processing the image signals.

In an example embodiment, the inspection apparatus may include an optical inspection apparatus in which the substrate may be inspected by using an optical beam having a wavelength larger than that of the electron beam and the defect imaging apparatus may include a scanning electron microscope (SEM).

According to example embodiments of the inventive concepts, a method of detecting defects of a substrate and making defect images thereof, the defects including a plurality of process defects that are randomly distributed on the substrate and at least a reference defect that may be defined at a reference area of the substrate, includes performing an inspection process, by an inspection apparatus, to the substrate to generate inspection positions of the defects on a basis of an inspection coordinate system, transferring the substrate onto a stage of a defect imaging apparatus, the defect imaging apparatus supporting an imaging coordinate system, converting, by defect imaging apparatus, the inspection positions of the defects in the inspection coordinate system to conversion positions of the defects in the imaging coordinate system, generating an imaging error based on a difference between a detected actual position and the conversion position of the reference defect, correcting the conversion positions of the process defects, respectively, by the imaging error, to generate irradiation positions corresponding to actual locations of the process defects, and generating image signals of the process defects by irradiating an electron beam to the irradiation position on the substrate.

In an example embodiment, the performing an inspection process may include using an optical beam having a wavelength larger than that of the electron beam.

In an example embodiment, the inspection process may be performed to a whole surface of the substrate such that the defects may be uniquely designated by the inspection positions, respectively, thereby generating a defect distribution map (DDM) onto which the defect on the substrate may be mapped by one to one.

In an example embodiment, the DDM may be generated as a binary file and be transferred to the defect imaging apparatus by one of a wired communication device and a wireless communication device.

In an example embodiment, the generating an imaging error may include searching for the reference defect on the substrate by moving a search window over the reference defect, aligning a center of the search window with a central position of the reference defect, selecting the center of the search window as the actual position of the reference defect, and obtaining the difference between the actual position and the conversion position by comparing the actual position and the conversion position of the reference defect.

In an example embodiment, when a size of a field of view of the search view may be greater than an allowable imaging error range, the search window may move over the reference detect with reference to the conversion position of the reference defect.

In an example embodiment, when a size of a field of view of the search view may be smaller than an allowable imaging error range, the search window may move over the reference defect with reference to a reference area of the reference defect.

In an example embodiment, when the at least one reference defect includes a plurality of reference defects, the generating an imaging error may further include performing a statistical process on a plurality of the differences between actual positions and conversion positions of some of the reference defects, and generating a statistically equivalent imaging error (SEIE) as the image error, the SEIE being a value at which a mean value of deviation from each of the differences is statistically minimized.

In an example embodiment, the method may further include searching for more reference defects to increase a population size for the statistical process, wherein the performing an statistical process includes repeatedly performing a statistical process on size-increased differences to generate an improved SEIE until an estimated reliability of the improved SEIE exceeds a threshold reliability value.

In an example embodiment, the electron beam may be irradiated to the irradiation position by controlling one of a beam irradiator from which the electron beam may be generated and the stage to which the substrate may be secured.

According to an example embodiment of the present inventive concepts, the reference defect RD may be intentionally provided on the reference area of the substrate W with a sufficient size for facilitating the detection. The actual position of the reference defect RD obtained by the detection may be compared the conversion position of the same reference defect RD, thereby generating the imaging error of the defect imaging apparatus, which may reduce the time and cost for generating the imaging error and may increase the accuracy of the imaging error.

For example, when a plurality of the inspection apparatuses and a plurality of the defect imaging apparatuses may be combined in a single defect detection system, the imaging error of the defect imaging apparatus may vary according to the pair of the inspection apparatus and the defect imaging apparatus. In such a case, the time and cost for the detection of the actual positions of a plurality of the reference defects and the generation of the imaging error of each pair of the apparatuses may be significantly reduced regardless of how many pairs of the inspection apparatus and the defect imaging apparatus are provided in the defect detection system.

Further, the automatic detection of the actual positions of the reference defect and the generation of the imaging error may facilitate the statistical treatment to a plurality of differences between a plurality of actual positions and a plurality of conversion positions of a plurality of the reference defects, thereby rapidly generating a more accurate imaging error.

According to an example embodiment of the present inventive concepts, a defect imaging apparatus includes a memory having computer-readable instructions stored therein; and at least one processor configured to execute the computer-readable instructions to receive inspection positions of defects on a substrate detected by an inspection apparatus, the defects including a plurality of random process defects and at least one reference defect defined at a reference area, the inspection positions being on a basis of a first coordinate system, convert the inspection positions of the defects in the first coordinate system to conversion positions of the defects in a second coordinate system, the second coordinate system being supported by the defect imaging apparatus, generate an imaging error based on a difference between an detected actual position and the conversion position of the reference defect, correct the conversion positions of the random process defects, respectively, based on the imaging error, to generate irradiation positions corresponding to actual locations of the random process defects, and generate image signals of the random process defects by irradiating an electron beam to each of the irradiation positions on the substrate.

In an example embodiment, the processor may be configured to execute the computer-readable instructions to generate the imaging error by searching the reference defect on the substrate by moving a search window over the reference defect, aligning a center of the search window with a central position of the reference defect, selecting the center of the search window as the actual position of the reference defect, and obtaining the difference between the actual position and the conversion position by comparing the actual position and the conversion position of the reference defect.

In an example embodiment, wherein when the at least one reference defect includes a plurality of reference defects, the processor may be configured to execute the computer-readable instructions to generate the imaging error by further performing a statistical process on a plurality of the differences between actual positions and conversion positions of some of the reference defects, and generating a statistically equivalent imaging error (SEIE) as the image error, the SEIE being a value at which a mean value of deviation from each of the differences is statistically minimized.

In an example embodiment, wherein the processor may be further configured to execute the computer-readable instructions to generate an improved SEIE by repeatedly performing the statistical process with respect to more of the reference detects until an estimated reliability of the improved SEIE exceeds a threshold reliability value.

In an example embodiment, wherein the processor may be further configured to execute the computer-readable instructions to control at least one of an image signal generator or a stage such that an electron beam irradiated by the image signal generator is focused to the irradiation positions.

BRIEF DESCRIPTION OF THE DRAWINGS

These and other features of the inventive concepts will become more apparent by describing in detail example embodiments thereof with reference to the accompanying drawings of which:

FIG. 5 is a block diagram illustrating a detect detection system including the detect imaging apparatus shown in FIG. 1;

DETAILED DESCRIPTION

Figure 1:
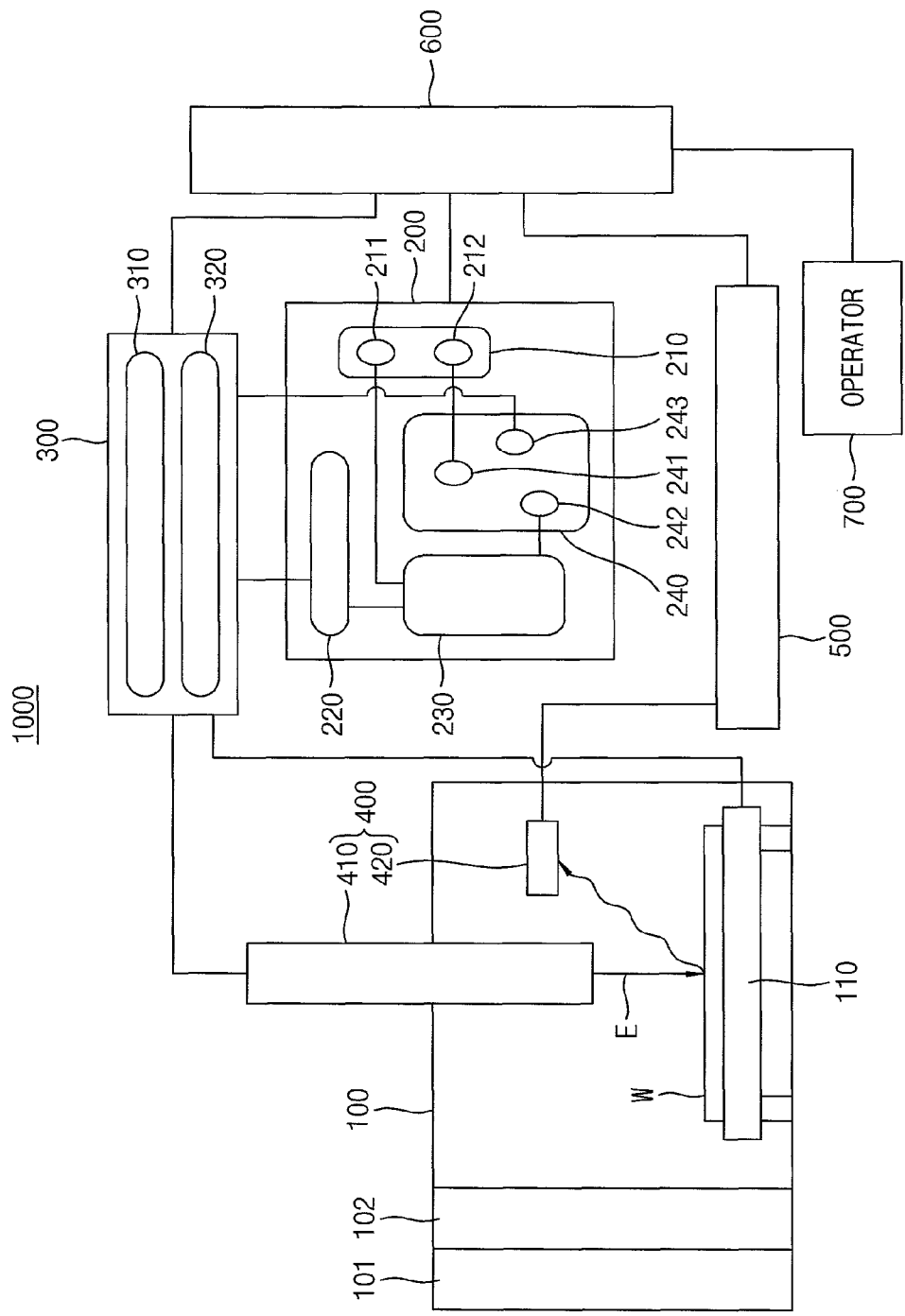
FIG. 1 is a block diagram illustrating a defect imaging apparatus in accordance with an example embodiment of the present inventive concepts.

Various example embodiments will now be described more fully with reference to the accompanying drawings. Example embodiments, however, may be embodied in many different forms and should not be construed as being limited to the example embodiments set forth herein. Rather, these example embodiments are provided so that this disclosure will be thorough and complete, and will fully convey the scope of the inventive concepts to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As used herein, the term "and/or" includes any and all combinations of one or more of the associated listed items. Expressions such as "at least one of," when preceding a list of elements, modify the entire list of elements and do not modify the individual elements of the list. Thus, for example, both "at least one of A, B, or C" and "A, B, and/or C" means either A, B, C or any combination thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein Reference will now be made to some example embodiments, which are illustrated in the accompanying drawings, wherein like reference numerals may refer to like components throughout.

FIG. 1 is a block diagram illustrating a defect imaging apparatus in accordance with an example embodiment of the present inventive concepts.

Referring to FIG. 1, a defect imaging apparatus 1000 may include a chamber 100, a position controller 200, an image signal generator 400, and an imaging device 500. The chamber 100 may include a stage 110, to which a substrate W having a plurality of randomly distributed process defects PD and at least one intentionally-provided reference defect RD is placed. The position controller 200 may automatically obtain an imaging error from an automatically detected actual position and a conversion position of the reference defect RD and correct a conversion position of the process defect PD by the equipment error, thereby generating an irradiation position at which the process defect is actually located. The image signal generator 400 may generate image signals of the process defect PD by irradiating an electron beam E to the irradiation position and detect charged particles discharged from the irradiation position in response to the electron beam. The imaging device 500 may make a defect image of the process defect PD by processing the image signals. The defect imaging apparatus 1000 may further include a scan controller 300 for aligning a beam generator with the irradiation position of the substrate W.

For example, the chamber 100 may have a vacuum inner space and the stage 110 may be provided at a bottom portion of the chamber 100. The substrate W may be loaded onto the stage 110 and may aligned with the stage 110. After the alignment, the substrate W may be secured to the stage 110. A load/lock chamber 102 may be provided with the defect image apparatus 1000 and the inner space of the chamber 100 may be under a desirable vacuum state, thereby minimizing the substrate contamination in the chamber 100. A substrate transfer device (not shown) such as a wafer cassette in which a plurality of the substrates W are stacked may be transferred onto a load port 101 of the defect imaging apparatus 1000 and the substrate W may be individually drawn out from the substrate transfer device at the load port 101 and may be loaded onto the stage 110 in the chamber 100 via the load/lock chamber 102.

In the present example embodiment, the chamber 100 may be enclosed by a sidewall to ensure the vacuum state and a cover (not shown) may be provided at a top portion of the chamber 100. The cover may be opened or closed as desired. A beam irradiator 410 may be inserted through the cover and may extend into the inside of the chamber 100, as will be described hereinafter.

The stage 110 may comprise non-magnetic materials so as to minimize or reduce the deflection of the electron beams E. The stage 110 may be accurately controlled by a mechanical operation. For example, a position feedback controller (not shown) such as a servo motor and a stepping motor may be provided with the stage 110, and thus the stage position may be accurately controlled in a real time when performing the defect imaging process in the chamber 100. In the present example, the stage 110 may be under the control of the scan controller 300, as will be described hereinafter, so that the stage position may be changed such that the electron beam E is accurately irradiated onto the irradiation position at which the process defect PD exists.

In the present example embodiment, the substrate W may include a semiconductor substrate to which a unit process of manufacturing processes for semiconductor devices may be performed. Thus, a plurality of fine pattern structures (not shown) may be arranged on the substrate W and a plurality of process defects may occur on the substrate as a result of the unit process.

Figure 2A:
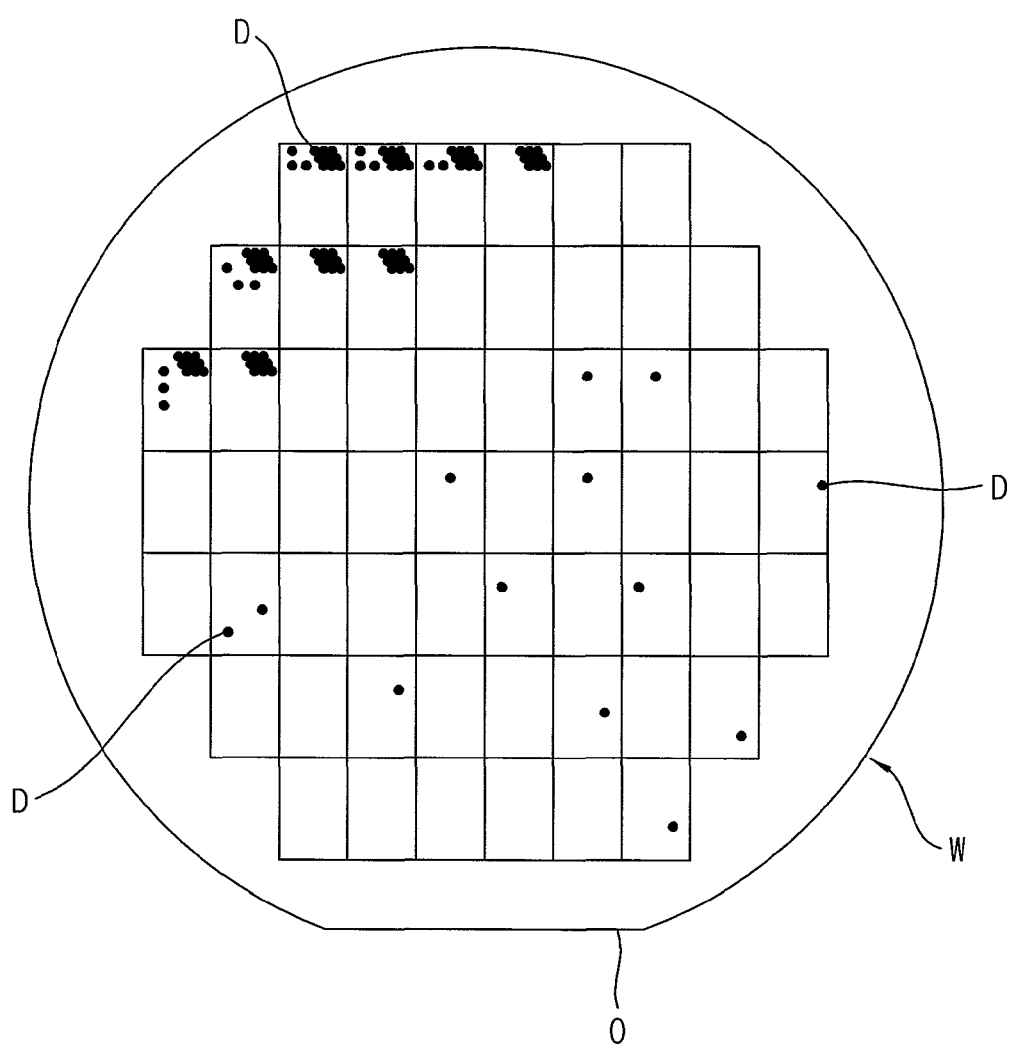
FIG. 2A is a plan view illustrating a substrate to which an example unit process for manufacturing semiconductor devices is completed.
Figure 2B:
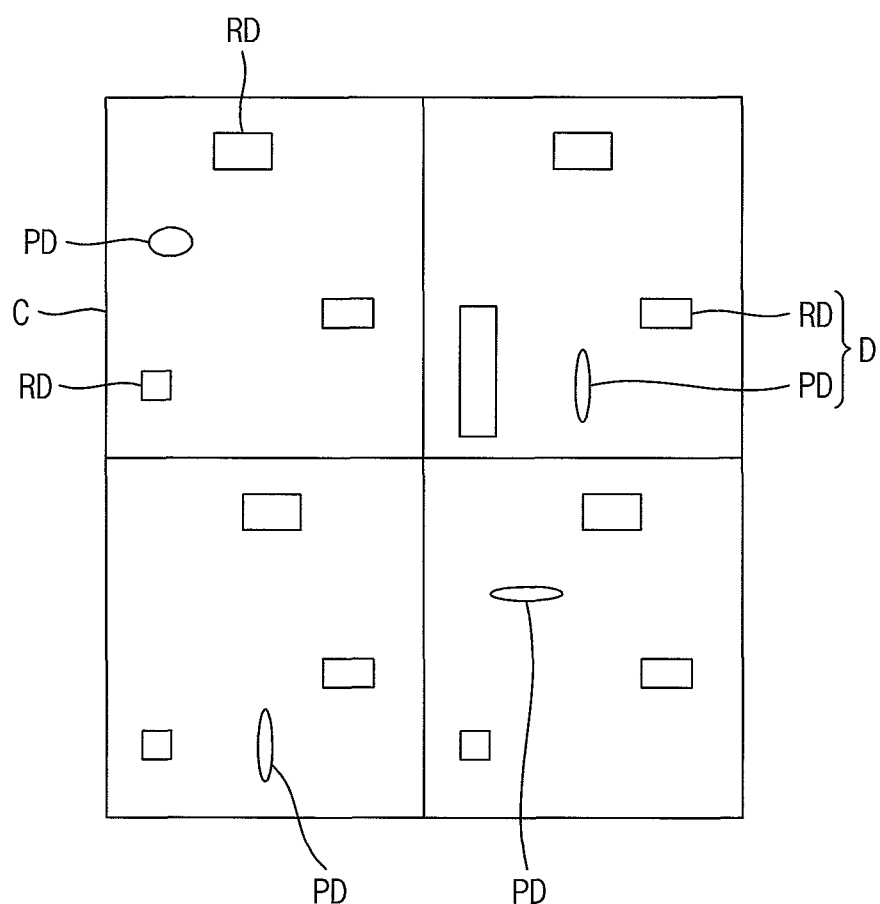
FIG. 2B is an enlarged view illustrating a chip of the substrate shown in FIG. 2A.

FIG. 2A is a plan view illustrating a substrate to which an example unit process for manufacturing semiconductor devices is completed, and FIG. 2B is an enlarged view illustrating a chip of the substrate shown in FIG. 2A.

Referring to FIGS. 2A and 2B a plurality of the process defects PD and at least a reference defect RD may be arranged on the substrate W. The process defect PD may be undesirably generated on the substrate W in the unit process of manufacturing processes for semiconductor devices, and thus the process defect PD may be randomly distributed on an entire surface of the substrate W. In contrast, the reference defect RD may be intentionally formed at a given area of the substrate W, and thus a plurality of the reference defects RD may be regularly and repeatedly arranged on the substrate W. The reference defects RD may be utilized for obtaining an imaging error of the defect imaging apparatus 1000.

For example, when performing a patterning process on a substrate W, a mother pattern for the reference defect RD may be formed on a reticle for the patterning process. Thus, the reference detect RD may be transcribed at a particular or a given area of the substrate W corresponding to the mother pattern, while the process defect PD may be undesirably formed on the substrate W in the patterning process.

The photolithography process may be performed along the entire surface of the wafer by using the reticle as a mask pattern. Thus, the reference defects RD may be repeatedly formed at every chip C along an entire surface of the substrate W, while the process defect PD may be selectively and individually generated by at least some of the unit chips C according to process conditions of each of the unit chips C. Therefore, the process defects PD may be randomly formed on the substrate W while the reference defects RD may be formed at a particular or a given area of the substrate W. As a result of the unit process, the defects D including the intentional reference defects RD and the undesired process defects PD may be arranged on the entire surface of the substrate W.

Because the mother pattern for the reference defect RD may be arranged at a designated point of the reticle, the reference defect RD may be formed at particular area (referred to as reference area) of the substrate W. In contrast, the process defects PD may be positioned at a random area/point of the substrate W. When the substrate W is optically inspected by a unit of pixel binning, the bin area of the pixel binning may be used as the reference area.

For example, the reference detect RD may have a sufficient size for detecting through a minimal field of view (FOV) of an object lens of the defect imaging apparatus 1000. The size of the reference defect RD may vary according to the size of the mother pattern and the optical characteristics of the photolithography process. For example, the reference detect RD may have a size sufficiently large for detection through a native resolution of the object lens.

In the present example embodiment, the size of the reference defect RD may be in a range of about 100 nm to about 900 nm and the FOV of the search window may be in a range of about 3×3 μm to about 5×5 μm.

While the process defect PD may have a size between a few nanometers and a few tens of nanometers due to a recent trend of higher degree of integration, the reference defect RD may have a size of about a few hundreds of nanometers for facilitating the detection through the search window of the object lens. A sufficiently large size of the reference defect RD at the given area, (e.g., the reference area) of the substrate W may facilitate accurate and easy detection of the reference defect RD. For example, the relatively large size of the reference area of the substrate W may enable the defect imaging apparatus 1000 to automatically detect the reference defect RD.

Prior to the defect imaging process, an inspection process may be performed to the substrate W in an inspection apparatus (not shown) and the position of the defect D may be obtained as a result of the inspection process. Hereinafter, the positions of the defects D, which are detected in the inspection apparatus on a basis of an inspection coordinate system may be referred to as an inspection position. The inspection positions of the defects D may be transferred to the defect imaging apparatus 1000 and may be utilized as basic information for identifying the defects D. That is, the target position of the electron beam E may be determined by manipulating the inspection position.

In the present example embodiment, the inspection apparatus may generate a defect distribution map (DDM) in which the defects D are uniquely designated by the inspection position. The defects D on the substrate W may be mapped onto the DDM by an one-to-one correspondence, and may be individually identified by the inspection positions. The DDM may be transferred to the defect imaging apparatus 1000.

The inspection apparatus may have a relatively low resolution and may scan the entire surface of the substrate W at a relatively high speed. Thus, the inspection position may designate all defects D on the substrate W based on the inspection coordinate system. In contrast, the defect imaging apparatus 1000 may have a relatively high resolution and may scan a specific local area of the substrate W at a relatively low speed based on the imaging coordinate system. To identify the defects D in the defect imaging apparatus 1000 by using the DDM based on the inspection coordinate system, coordinate conversion between the inspection coordinate system and the imaging coordinate system may be conducted in the defect imaging apparatus 1000.

Further, the inspection apparatus and the defect imaging apparatus 1000 may be individually and independently operated under a respective operation and instrumental errors. Thus, the inspection position of the DDM may also be corrected in view of the operation and instrumental errors for identifying the defects D in the defect imaging apparatus 1000 by using the DDM.

The position controller 200 may convert the inspection position into a conversion position of the defect D by the coordinate conversion and may correct the conversion position in view of the operation and instrumental errors of inspection apparatus and the defect imaging apparatus 1000.

Thus, the defect D on the substrate W may be accurately designated in the defect imaging apparatus 1000 based on the DDM.

Besides the conversion position due to the coordinate conversion, the defect imaging apparatus 1000 may actually search for the reference detect RD, not the process defect, and may detect an actual position of the reference defect RD on a basis of the imaging coordinate system. Thereafter, the conversion position and the actual position of the reference defect RD may be compared with each other. The difference between the actual position and the conversion position of the reference defect RD may be selected as an imaging error of the defect imaging apparatus 1000. The conversion position of the process defect PD on the substrate W may be corrected by this imaging error (e.g., an equipment error of the defect imaging device 1000), thereby generating an irradiation position at which the process defects PD be actually located. The electron beam E may be irradiated to the irradiation position, thereby generating the defect image of the process defect PD.

In an example embodiment, the position controller 200 may include a conversion unit 210, a search unit 220, an error generator 230, and a correction unit 240. The conversion unit 210 converts the inspection position on the DDM to the conversion position by the coordinate conversion. The search unit 220 searches for the reference defect RD on the substrate W and automatically detects the actual position of the reference defect RD on a basis of the imaging coordinate system. The error generator 230 generates the imaging error as the difference between the actual position and the conversion position of the reference defect RD. The correction unit 240 corrects the conversion position of the process defect PD by the imaging error to thereby generate the irradiation position of the process defects PD.

When completing the inspection process in the inspection apparatus, the DDM may be transferred to the conversion unit 210 of the defect imaging apparatus 1000 from the inspection apparatus as, for example, a binary file.

The conversion unit 210 may be connected to an operator 700 via a central control console 600. A user interface such as a storage driver may be provided with the operator 700. A portable storage may be inserted into the storage driver of the operator 700 and the DDM file may be transferred to the conversion unit 210 through the operator 700 under the control of the central control console 600. Otherwise, the DDM file may be transferred to the conversion unit 210 from the inspection apparatus through a wired/wireless communication.

When the substrate W is aligned with the stage 110 of the chamber 100, the imaging coordinate system may be set up and a point of the substrate W may be selected as the origin of the inspection coordinate system and as an origin of the imaging coordinate system. For example, a reference point O in FIG. 2A of the substrate W may be used as the origin of the coordinate systems. Then, the conversion unit 210 may perform, using a coordinate conversion algorithm, mathematical coordinate conversion between the inspection and the imaging coordinate systems in. Thus, the inspection position may be converted into the conversion position by the coordinate conversion algorithm. The conversion position of the reference defect RD may be stored into a first storing section 211 and the conversion position of the process defect may be stored into a second storing section 212.

The coordinate value of the same reference point O may be different in the inspection apparatus and in the defect imaging apparatus 1000 due to an alignment error of the substrate W and/or the resolution difference between the inspection apparatus and the defect imaging apparatus 1000. The coordinate conversion may compensate for the alignment error and the resolution difference between the inspection apparatus and the defect imaging apparatus 1000.

While the present example embodiment discloses a case where the corner point of a flat zone of a wafer is used as the origin of the coordinate system, any other points of the wafer may also be used as the origin of the coordinate system in view of the alignment accuracy and the detection accuracy of the inspection apparatus and the defect imaging apparatus 1000.

In spite of the mathematical coordinate conversion, the conversion position of the defect D may not coincide with an actual position of the defect D due to various errors of the inspection apparatus and the defect imaging apparatus 1000. Thus, the conversion position of the defects D may be desired to be adjusted to further compensate for the errors.

For example, because the inspection position of the defect D is obtained by an operation of the inspection apparatus, the inspection position of the defect D may include inherent operation errors and instrumental errors of the inspection apparatus. Likewise, because the defect image of the process defect PD is obtained by an operation of the defect imaging apparatus 1000, the target position of the beam irradiator 410 may be deviated from an actual position of the process defect PD due to the inherent operation errors of the beam irradiator 410 and/or the stage 110, and/or the instrumental errors of the defect imaging apparatus 1000.

Therefore, the deviation between the target position of the beam irradiator 410 and the actual position of the process defect PD may be amplified by an accumulation of the inherent errors of the inspection apparatus and/or the defect imaging apparatus 1000. In the present example embodiment, the inherent operations and instrumental errors (equipment error) of the inspection apparatus and the defect imaging apparatus may be corrected at a time based on a calculated imaging error. Thus, the electron beam E may be accurately focused to the actual position of the process defect PD in the defect imaging apparatus 1000. The imaging error may be calculated by using the position of the reference defect RD.

The search unit 220 may move a search window SW over the reference area of the substrate W and may detect the reference defect RD. In such a case, because the reference defect RD may be located at a known area (e.g., the reference area) of the substrate W, the search unit 220 may be rapidly detect the reference defect RD. Then, the center SC of the search window may be aligned with the central position of the reference defect RD, thereby automatically detecting the actual position of the reference defect RD.

Then, the conversion position and the actual position of the reference defect RD may be compared in the error generator 230 and the difference between the conversion position and the actual position may be selected as the imaging error. Because the conversion position of the reference defect RD may inherently include the equipment error of the inspection apparatus and the actual position of the reference defect RD may inherently include the equipment of the defect imaging apparatus 1000, the imaging error may correct the misalignment of the target position of the electron beam E and the actual position of the process defect in the defect imaging apparatus in view of the equipment errors both of the inspection apparatus and of the defect imaging apparatus.

Figure 3:
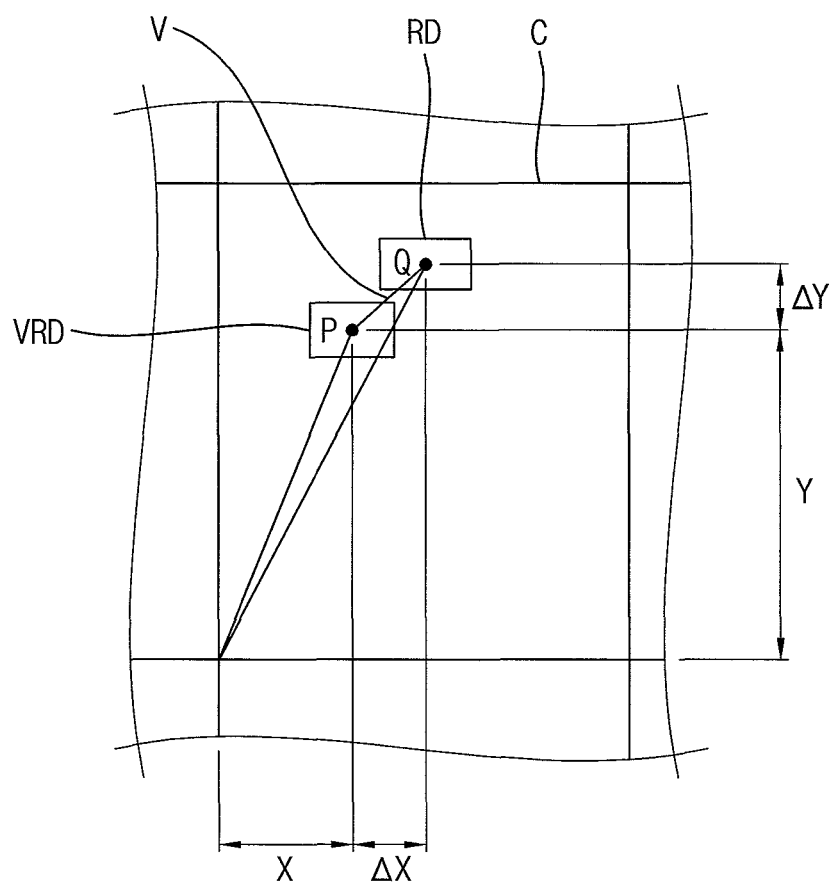
FIG. 3 is a view illustrating a position difference between the actual position and the conversion position of the reference defect on the substrate W in the defect imaging apparatus.

FIG. 3 is a view illustrating a position difference between the actual position and the conversion position of the reference defect on the substrate W in the defect imaging apparatus.

Referring to FIG. 3, the reference defect RD may be actually positioned at a point Q(x+Δx, y+Δy) in the defect imaging apparatus 1000. However, the reference defect RD may be at a point P(x, y) according to the coordinate conversion. Although the central position of the reference defect RD may be actually detected as the point Q in the defect imaging apparatus 1000, the coordinate conversion may indicate as if the central position of the reference defect RD is at the conversion position P. Hereinafter, the reference defect of which the central position may coincide with point P will be referred to as virtual reference defect VRD as compared with the actual reference defect RD. Accordingly, the deviation between the points P and Q, which may be denoted as Δx in a latitudinal direction and as Δy in a longitudinal direction, may be selected as the imaging error of the defect image apparatus 1000.

Conventionally, the reference defect RD may be manually searched from the substrate W and the central position of the reference defect RD may also be manually detected by an operator. In contrast, the search unit 220 may search (e.g., automatically) the reference defect RD on the substrate W and detect (e.g., automatically) the central position of the reference defect RD, thereby obtaining (e.g., automatically), using for example a processor configured to perform a mathematical algorithm, the imaging error in the defect imaging apparatus 1000.

Figure 4A:
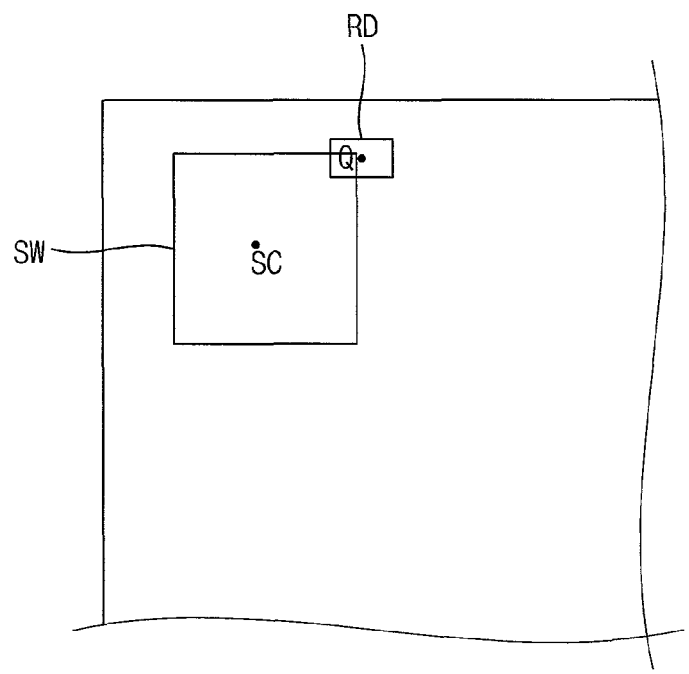
FIG. 4A is a view illustrating a search window moving toward the reference defect of the substrate W in the defect imaging apparatus.
Figure 4B:
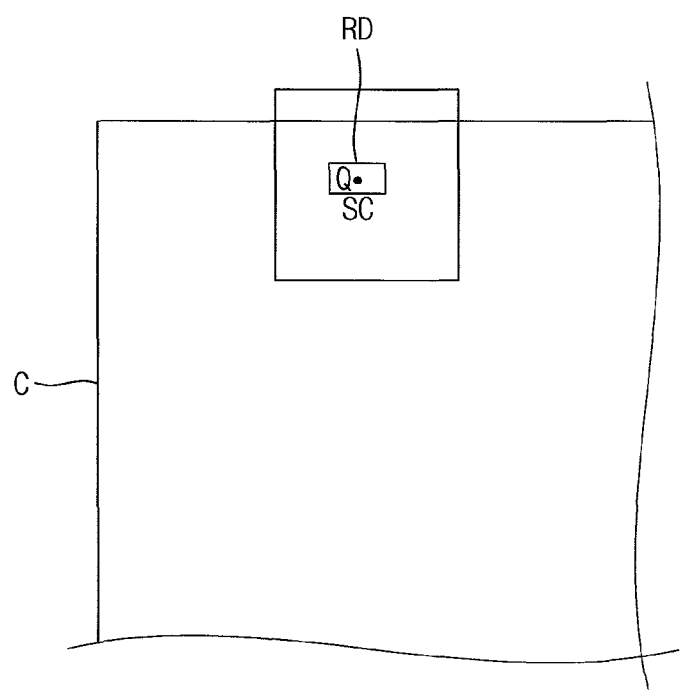
FIG. 4B is a view illustrating the search window aligning with the reference defect of the substrate W in the defect imaging apparatus.

FIG. 4A is a view illustrating a search window moving toward the reference defect of the substrate W in the defect imaging apparatus and FIG. 4B is a view illustrating the search window aligning with the reference defect of the substrate W in the defect imaging apparatus.

Referring to FIGS. 4A and 4B, when completing the alignment of the substrate W with the stage 110 of the chamber 100, the central control console 600 may operate the search unit 220 in such a way that the search window SW of an object lens may move over the reference defect RD.

The central control console 600 may set up a field of view (FOV) of the search window SW in view of the equipment characteristics of the defect imaging apparatus 1000. In the present example embodiment, the reference detect RD may have a size of about 100 nm to about 900 nm and the search window SW may have a FOV shaped into a square of about 3 μm×3 μm to about 5 μm×5 μm. The size of the FOV may vary in accordance with the size of the reference defect RD.

Due to the automatic search of the reference defect RD, the reference defect RD may be sufficiently included in the FOV of the search window SW and the search unit 220 may detect an entire shape and size of the reference defect RD. Thereafter, the search window SW may be adjusted such that the center SC of the search window SW may be aligned with the central point Q of the reference defect RD.

When completing the center alignment between the search window SW and the reference defect RD, the coordinate value of the center of the search window SW may be selected as an actual position of the reference defect RD. In the present example embodiment, the coordinate value of the central point Q in FIG. 3A may be determined as the actual position of the referenced defect RD.

Accordingly, the automatic detection of the reference defect center may reduce the time and cost for obtaining the imaging error of the defect imaging apparatus 1000 as compared with the manual detection of the center of the reference defect in the conventional defect imaging apparatus.

The actual position of the reference defect RD may be transferred to the error generator 230 and may be compared with the conversion position of the reference defect RD in the error generator 230.

The conversion position of the reference detect RD may be transferred to the error generator 230 from the first storing section 211 of the conversion unit 210.

Because the conversion position is generated from the inspection position by executing the mathematical coordinate conversion algorithm in the conversion unit 210, the deviation between the actual position and the conversion position may be caused by the equipment errors of the inspection apparatus and/or the defect imaging apparatus. Thus, the deviation between the conversion position and the actual position may indicate a correction value and/or the imaging error for correcting the equipment errors of the inspection apparatus and the defect imaging apparatus, thereby accurately generating the defect image of the actual reference defect RD in the defect image apparatus 1000.

In the present example embodiment, the inspection position and the conversion position may be expressed in a Cartesian coordinate system and the imaging error may include x and y components.

For example, the imaging error of the reference defect RD in FIG. 3 may include an error vector V having an x component of Δx and a y component Δy.

Because the imaging error may include the operational characteristics and the instrumental characteristics of the inspection apparatus and the defect imaging apparatus 1000, the error vector V may be applied to all defects D on the substrate W unless the configurations of the apparatus are changed. That is, the imaging error may be an apparatus-dependent constant that may vary by the inspection apparatus and/or the defect imaging apparatus. Further, the error vector V may be effective regardless of a substrate and thus the defect image may be obtained from a plurality of the substrates by using the same error vector V unless the apparatus characteristics are changed.

Therefore, the imaging error may be constant and effective regardless of the substrate W including the process defect PD as long as the configurations and the characteristics of the inspection apparatus and/or the defect imaging apparatus 1000 do not change.

To enhance the accuracy of the imaging error, a plurality of the error vectors V may be obtained from a plurality of reference defects RD, respectively. An overall error vector may be generated by mathematical and/or statistical treatments as a single imaging error.

For example, five chips including left and right chips, top and bottom chips and a central chip may be picked up from the substrate W, and five reference defects RD may be individually searched for by the search unit 220. Thus, five error vectors V may be generated from the five chips, respectively. Then, a statistical treatment (e.g., a linear regression process) may be applied to five x components of the error vectors to generate a single equivalent x component and to five y components of the error vectors to generate a single equivalent y component. Accordingly, a single equivalent error vector that may have the equivalent x and y components and be statistically close five error vectors may be obtained as the imaging error of the defect imaging apparatus 1000.

The imaging error may be transferred to the correction unit 240 and the correction unit 240 may correct the conversion position of the process defect PD by the imaging error. Thus, the corrected conversion position of the process defect PD may be used as an irradiation position corresponding to an actual location of the process defect PD. Thus, the electron beam E for generating the defect image of the process defect PD may be irradiated to the irradiation position.

For example, the correction unit 240 may include components such as a first buffer 241, a second buffer 242, and a coordinate corrector 243. The first buffer 241 may receive the conversion position of the process defect PD transferred from the second storing section 212. The second buffer 242 may receive the imaging error transferred from the error generator 230. The coordinate corrector 243 may correct the coordinate value of the conversion position of the process defect PD by the imaging error, and generate the irradiation position corresponding to an actual location of the process defect PD.

The first buffer 241 may be connected to the second storing section 212 and the second buffer 242 may be connected to the error generator 230. In the present example embodiment, when the coordinate correction is initiated to correct the conversion positions of process defect PD, the central control console 600 may transfer the conversion positions of the process defects PD to the first buffer 241 from the second storing section 212 and may transfer the imaging error to the second buffer 242 from the error generator 230.

The coordinate corrector 243 may change the coordinate values of the conversion position of the process defect PD by the imaging error through, for example, a linear mapping, thereby generating the irradiation position corresponding to the process defect PD. In the linear mapping, the x and y components of the conversion position of the process defect PD may be linearly translated, respectively, by the x and y components of the error vector V.

Therefore, the irradiation position may accurately designate the actual process defect PD in the defect imaging apparatus 1000 on a basis of the imaging coordinate system. When the electron beams E is irradiated onto the irradiation position of the substrate W, an image of the process detect PD may be accurately taken into in the defect imaging apparatus 1000. For example, the irradiation position may be automatically obtained by the position controller 200 and the reference defect RD. Thus, the defect image of the process defect PD may be more efficiently and accurately generated.

The scan controller 300 may be connected to the position controller 200 and may control the electron beam E to be focused to the irradiation position. In the present example embodiment, the scan controller 300 may control at least one of the beam irradiator 410 or the stage 110 such that the beam irradiator 410 of the image signal generator 400 is aligned with the irradiation position of the substrate W corresponding to an actual location of the process defects PD.

In the present example embodiment, the scan controller 300 may include an irradiator controller 310 and a stage controller 320. The irradiator controller 310 may generate the electron beams E at the beam irradiator 410 and control the configurations of the beam irradiator 410. The stage controller 320 may control the position of the stage 110.

For example, the beam irradiator 410 may be aligned with the irradiation position on the substrate W by the scan controller 300. When the scan controller 300 receives the irradiation position, the beam irradiator 410 and/or the stage 110 may be moved by the scan controller 300 such that the beam irradiator 410 is accurately aligned with the process defect PD.

The scan controller 300 may be connected to the central control console 600 like the position controller 200 and the scan controller 300 may be operated in relation with the position controller 200 by the central control console 600. When the irradiation position of the process defect PD is generated, the central control console 600 may operate the error generator 230 to transfer the irradiation position to the scan controller 300 as, for example, a binary file and may apply an operation signal to the scan controller 300. Accordingly, the automatic generation of the irradiation position of the process defects PD and the automatic alignment of the beam generator 410 with the irradiation position may be carried out by the central control console 600, thereby increasing accuracy and efficiency of the defect image of the process defect PD.

The image signal generator 400 may irradiate the electron beams E to the irradiation position on the substrate W and detect the charged particles that may be generated from the irradiation position in response to the electron beam E, thereby generating image signals corresponding to the process defect PD.

For example, the image signal generator 400 may include abeam irradiator 410 for irradiating the electron beams E to the substrate W and a detector 420 for detecting the charged particles. The detector 420 may generate the image signal of the process defect PD corresponding to the irradiation position by processing the detected charged particles.

The beam irradiator 410 may be arranged at an upper portion of the chamber 100. In the present example embodiment, the beam irradiator 410 may include an electron gun penetrating through atop cover (not shown) of the chamber 100, a deflection lens, and a coil for controlling the path of the electron beam E. The electron beam E may be irradiated onto the substrate W along a uniform beam path with a uniform intensity.

The stage 110 may be located at a stationary position in the chamber 100 and the beam irradiator 410 may move over the substrate W until the beam irradiator 410 is aligned with the irradiation position. When the beam irradiator 410 is aligned, the electron beams E may be irradiated onto the irradiation position on the substrate W. In contrast, the beam irradiator 410 may be located at a stationary position over the substrate W in the chamber 100 and the stage 110 may move in 3-dimensional directions until the substrate W may be aligned with the beam irradiator 410 and the beam path and an irradiation angle of the electron beams E may be directed to the irradiation position.

The charged particles (e.g., secondary ions) may be generated from the substrate W corresponding to the irradiation position and the detector 420 may detect the charged particles and generate image signal of the process defect PD, which is located at the irradiation position of the substrate W.

The image signal may be amplified in an amplifier (not shown) and may be transferred to the imaging device 500. The imaging device 500 may include an image generating unit (not shown) for processing the image signal and making an image of the process defect PD and an image storing unit (not shown) for storing the image of the process defect PD.

The image of the process defect PD may be visualized in the operator 700 by the central control console 600. For example, the operator 700 may include display unit (now shown) such as a monitor of a computer system and the operator may visually confirm the process defect PD on the monitor.

According to the example embodiments of the defect imaging apparatus 1000, the reference defect RD may be provided on the reference area of the substrate W with a size sufficient for the position controller 200 to easily and accurately detect the size and position of the reference defect RD. The inspection position of the defect D on the substrate W may be converted into the conversion position of the defect D in the position controller 200. Then, the actual position of the reference defect RD may be compared with the conversion position thereof and the difference between the actual position and the conversion position of the reference defect RD may be obtained as the imaging error of the defect imaging apparatus 1000. The conversion position of the process defect PD may be corrected by the imaging error, to thereby obtain the irradiation position corresponding to an actual location of the process defects PD. The electron beam E may be irradiated onto the irradiation position and the image signal corresponding to the process defect PD may be generated from the irradiation position. Accordingly, the defect imaging apparatus 1000 may automatically and accurately generate the defect image of the process defect PD by correcting the inspection position of the process defect PD by the imaging error.

FIG. 5 is a block diagram illustrating a defect detection system including the defect imaging apparatus shown in FIG. 1.

Referring to FIGS. 1 and 5, the defect detection system 2000 in accordance with an example embodiment of the present inventive concepts may include a port 1100, at least an inspection apparatus 1200, at least a defect imaging apparatus 1300, and a transfer member 1400. The port 1100 may provide a substrate having a plurality of process defects PD and at least a reference defect RD for detecting the process defects PD, The at least an inspection apparatus 1200 may inspect the substrate W loaded from the port 1100, and generate positions of the process defects PD and the reference defect RD as inspection positions thereof. The at least a defect imaging apparatus 1300 may receive the substrate W from the inspection apparatus 1200 and generate an image of the process defect PD. The transfer member 1400 may transfer the substrate W among the port 1100, the inspection apparatus 1200 and the defect imaging apparatus 1300.

A unit process of manufacturing processes for semiconductor devices may be carried out on the substrate W and various defects D may be formed on the substrate W. The defects D may include the reference defect RD that is intentionally formed on the reference area of the substrate W and the process defect PD that may be undesirably formed and may be arbitrarily arranged on the substrate W. When the unit process of the manufacturing processes is completed, a plurality of the substrates W may be stacked on a substrate transfer device such as a wafer cassette and the substrate transfer device may move into the port 1100 of the defect detection system 2000. Thus, a plurality of the substrates W may be transferred to the defect detection system 2000 at a time. In some example embodiments, a single substrate W may be transferred to the port 1100 of the defect detection system 2000.

The defect image may require a high resolution for an accurate examination of the defect. Thus, a short wavelength beam such as the electron beam E may be used for detecting the defect D. However, the inspection of the entire surface of the substrate W by the short wavelength beam may take a longer inspection time due to the short wavelength. According to the example embodiments, the inspection time may be reduced by (1) firstly detecting the position of a defect D along an entire surface of the substrate W at a relatively high speed by using an optical beam having a wavelength relatively longer than that of the electron beam E, and (2) then generating the image of the defect D from a local area of the substrate W, at which the defect D is present, at a relatively low speed by using the short wavelength beam.

Based on the above detection guidelines, the substrate W may be picked up individually from the substrate transfer on the port 1100 and may be loaded into the inspection apparatus 1200. An optical inspection process may be performed on the substrate W at a relatively high speed in the inspection apparatus 1200 and the position of the defect D may be rapidly detected on a basis of the inspection coordinate system, thereby obtaining the inspection positions of all defects D. The inspection positions may correspond to the defects D on the substrate W, respectively, thereby forming the defect distribution map (DDM). The DDM may be provided as a binary file and may be transferred to the defect imaging apparatus 1300 by a wired/wireless communication.

The inspection position may be converted by a coordinate conversion from the inspection coordinate system to the imaging coordinate system. Thus, the inspection positions of the reference defect RD and the process defects PD may be converted into the conversion positions thereof. For example, the reference defect RD may be actually searched and detected in the defect imaging apparatus 1000 to thereby obtain the actual position of the reference defect RD and then the actual position of the reference defect RD may compared with the conversion position of the reference defect RD. The difference between the actual position and the conversion position of the reference defect RD may be stored as the imaging error of the defect imaging apparatus 1300. Then, the conversion positions of the process defects PD may be corrected by the imaging error, to generate the irradiation positions corresponding to an actual location of the process defects PD. The electron beam E may be irradiated onto the irradiation position of the substrate W and the defect image of the process defect PD may be accurately generated in the defect imaging apparatus 1300. The electron beam E may increase the resolution of the defect image as compared with the optical beam of the inspection apparatus 1200 while the scanning speed of the electron beam E may be lower than that of the optical light.

Referring to FIGS. 1 and 5. The defect imaging apparatus 1300 may include the position controller 200 for generating the irradiation positions of the process defect PD that are corrected by the imaging error, the scan controller 300 for focusing the electron beam E to the irradiation position of the substrate W, the image signal generator 400 irradiating the electron beam E to the irradiation position and generating image signal by detecting the charged particles in response to the electron beam E, and the imaging device 500 for generating the defect image by processing the image signal.

The defect imaging apparatus 1300 may have the same or similar structures as the defect imaging apparatus 1000 shown in FIG. 1, and thus any further detailed descriptions on the defect imaging apparatus 1300 will be omitted.

In the present example embodiment, the inspection apparatus 1200 may include an optical inspection apparatus in which an optical beam having a wavelength longer than that of the electron beam E may be used for inspecting the substrate W and the defect imaging apparatus 1300 may include a scanning electron microscope (SEM) apparatus.

According to an example embodiment of the defect detection system 2000, the substrate W having the reference defect RD and the process defect PD may be firstly inspected by the optical beam and the inspection positions of the reference and process defects RD and PD may be generated in the inspection apparatus. Then, the substrate W may be loaded into the defect imaging apparatus and the defect image of the process defect PD may be generated by the electron beam E. The reference defect RD may be automatically detected in the defect imaging apparatus and the difference between the conversion position and the actual position of the reference defect RD may be generated as the imaging error of the defect imaging apparatus. The conversion positions of the process defects PD may be automatically corrected and used as the irradiation positions and the electron beam E may be irradiated onto the irradiation positions of the substrate W. Thus, the defect image corresponding to the process defect PD may be generated with higher accuracy and efficiency.

For example, three inspection apparatuses 1210 to 1230 and two defect imaging apparatuses 1310 and 1320 may be simultaneously operated in the defect detection system 2000, so the defect detection may be performed to a plurality of the substrates at the same time.

In such a case, the inspection apparatuses 1210 to 1230 and the defect imaging apparatuses 1310 and 1320 may have their own equipment error, and the apparatus-dependent imaging error may vary according to the inspection apparatus and/or the defect imaging apparatus. In the present example embodiment, the defect detection system 2000 may have six different pairs of combinations between the inspection apparatus 1200 and the defect imaging apparatus 1300, and thus may have 6 different imaging errors.

Therefore, the more the pairs of the inspection apparatus and the defect imaging apparatus, the longer the time for obtaining the imaging errors. As the number of the unit processes of the manufacturing process may increase due to the high integration degree of the semiconductor devices, the defect detection system 2000 may require a larger number of the pairs of the inspection apparatus and the defect imaging apparatus for reducing the defect detection time. According to conventional manual detection methods, manual detection of the actual position of the reference defect may take a relatively much longer time for generating the imaging errors corresponding to each pair of the inspection apparatus and the defect imaging apparatus, Thus, overall efficiency of the manufacturing process for semiconductor devices may be significantly decreased.

However, according to the present example embodiment of the defect detect system, the actual position of the reference defect may be automatically detected in the defect imaging apparatus and the imaging error may be automatically and rapidly generated no matter how many pairs of the inspection apparatus and the defect imaging apparatus may be provided in the defect detection system 2000. Accordingly, efficiency of the defect detection may significantly increase when a plurality of the inspection apparatuses and the defect imaging apparatuses are provided with the defect detection apparatus 2000.

The aforementioned components of the defect imaging apparatus 1000 (e.g., the conversion unit 210, the search unit 220, the error generator 230, the correction unit 240, the coordinate corrector 243, the scan controller 300, and/or the stage controller 320) may be implemented by a memory (not shown) and at least one processor (not shown). The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the defect imaging apparatus as a special purpose computer. The instructions may be stored on a non-transitory computer readable medium (e.g., memory). Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

The aforementioned components of the defect imaging apparatus 1000 described herein may be implemented using hardware components and/or a combination of hardware and software components. For example, the hardware components may include microphones, amplifiers, band-pass filters, audio to digital convertors, and processing devices.

A processing device may be implemented using one or more hardware devices configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and/or one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and/or multiple types of processing elements. For example, a processing device may include multiple processors or a processor and a controller. Further, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

Hereinafter, the method of defect detection will be described in detail on a basis of the defect detection system 2000 shown in FIG. 5.

Figure 6:
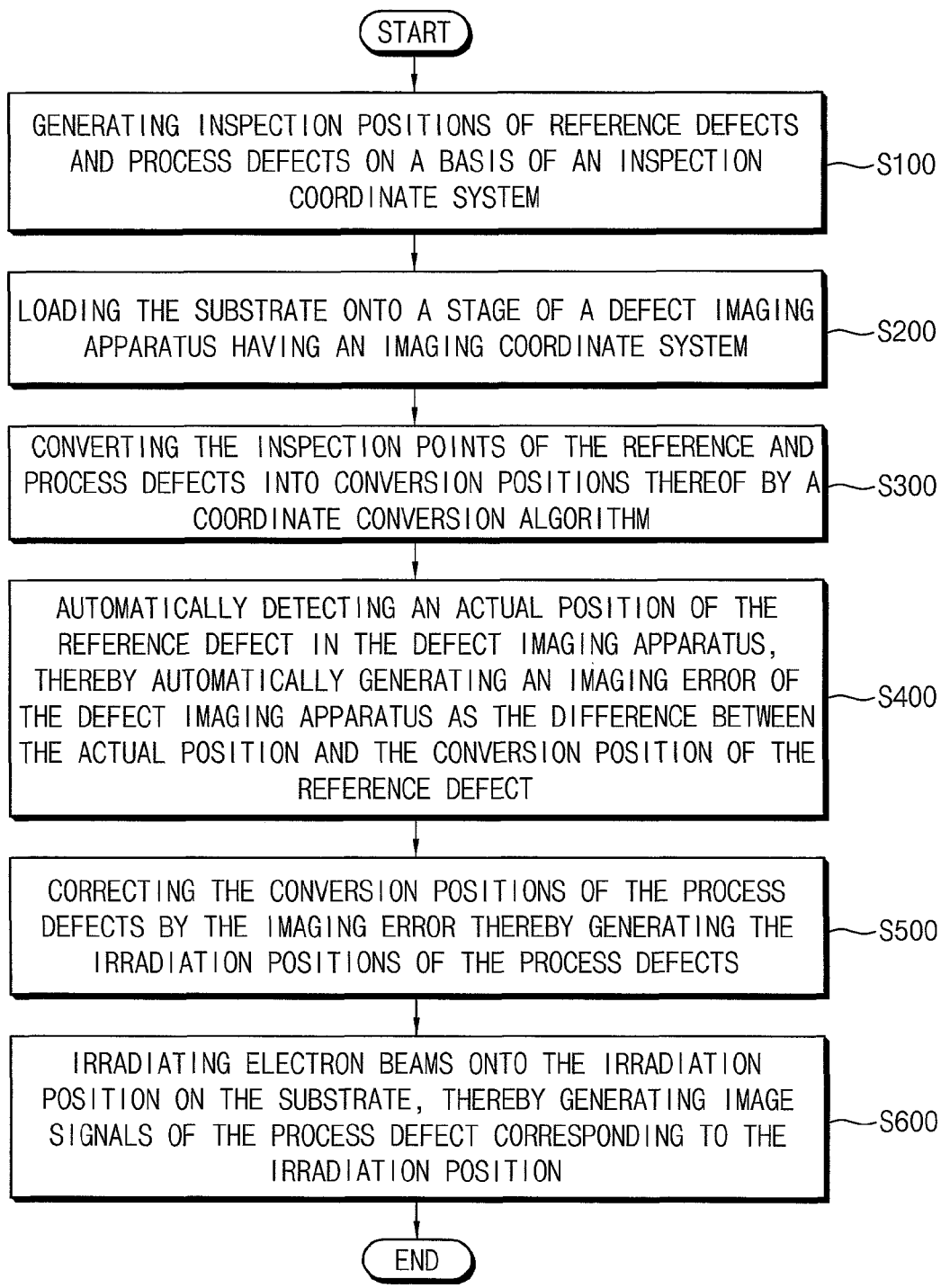
FIG. 6 is a flow chart showing process steps for a method of detecting defects in the defect detection system shown in FIG. 5.

FIG. 6 is a flow chart showing process steps for a method of detecting defects in the defect detection system shown in FIG. 5.

Referring to FIGS. 1, 5 and 6, an inspection process may be carried out on the substrate W having a plurality of the process defects PD and at least a reference defect RD in the inspection apparatus 1200 and the inspection positions of the process detects RD and the reference defect RD may be generated on a basis of the inspection coordinate system (step S100).

When the unit process of the manufacturing process for semiconductor devices is completed, an optical inspection process may be carried out on the substrate W having the process defects PD and at least a reference defect RD in the inspection apparatus 1200, and the positions of all reference defects RD and process defects PD may be generated along an entire surface of the substrate W, thereby generating the defect distribution map (DDM) of the substrate W.

The reference detect RD may be intentionally formed at the reference area of the substrate W with a size sufficient for an easy and rapid detection and the process defect PD may be undesirably formed on the substrate W. For example, the reference defect RD may be regularly arranged at the desired (or alternatively, predetermined) reference area of the substrate W and the process defects PD may be randomly arranged on the substrate W when the unit process is completed. For example, the mother pattern of the reference defect RD may be provided at a mask pattern for a patterning process and thus the reference defect RD may be arranged at the same position at every chip on the substrate W.

The inspection coordinate system may be selected in view of the resolution of the optical beam of the inspection apparatus 1200 and a particular point such as the reference point O of the substrate W may be set up as an origin of the inspection coordinate system. The defects D on the substrate W may be uniquely designated by the inspection positions in the inspection coordinate system. The inspection positions of the defects D may be formed into a defect distribution map (DDM) as, for example, a binary file.

When the inspection process to the substrate W is completed, the substrate W may be transferred to the defect imaging apparatus 1300. The substrate W may be loaded onto the stage 110 of the chamber 100 in the defect imaging apparatus 1300, which has the imaging coordinate system (step S200). In such a time, The DDM may be transferred to the conversion unit 210 of the position controller 200 of the defect imaging apparatus 1300.

For example, the flat zone of the substrate W may be aligned with a reference line of the stage 110 and the same reference point O of the substrate W may be set up as an origin of the imaging coordinate system. The imaging coordinate system may be selected in view of the resolution of the electron beam of the defect imaging apparatus 1300.

Then, the inspection positions of the defects D on a basis of the inspection coordinate system a be converted into the conversion positions thereof on a basis of the imaging coordinate system by the coordinate conversion algorithm (step S300).

When the imaging coordinate system is set up in the defect imaging apparatus 1300, the conversion unit 210 may perform a mathematic coordinate conversion algorithm, thereby automatically converting the inspection positions of the DDM into the conversion positions in the imaging coordinate system.

The conversion positions of the reference defect may be stored in the first storing section 211 and the conversion positions of the process defect PD may be stored in the second storing section 212.

Because the conversion positions of the defects D is mathematically generated by the coordinate conversion algorithm, the actual position of the process defect PD may be deviated from the conversion position thereof by the imaging error, which is caused by the equipment errors of apparatuses 1200 and/or 1300.

The actual position of the reference defect RD in the defect imaging apparatus 1300 may be automatically detected by the search unit 220 of the position controller 200 and the difference between the actual position and the conversion position of the reference defect RD may be automatically generated as the imaging error of the defect imaging apparatus 1300 (step S400).

When the alignment of the substrate W with the stage 110 of the chamber 100 is completed, the search window SW may move over the reference defect RD located at the reference area of the substrate W. Then, the center SC of the search window SW may be aligned with the central position of the reference defect RD, and the actual position of the reference defect RD may be detected. Thereafter, the difference between the actual position and the conversion position of the reference defect RD may be generated as the imaging error of the defect imaging apparatus 1300.

For example, because the reference defect RD has a sufficiently large size, the search unit 220 may easily detect the reference defect RD by adjusting the FOV of the object lens. Further, because the reference defect RD is intentionally formed at the desired (or alternatively, predetermined) area of the substrate W, the reference defect RD may be automatically and rapidly searched by the search unit 220.

Figure 7:
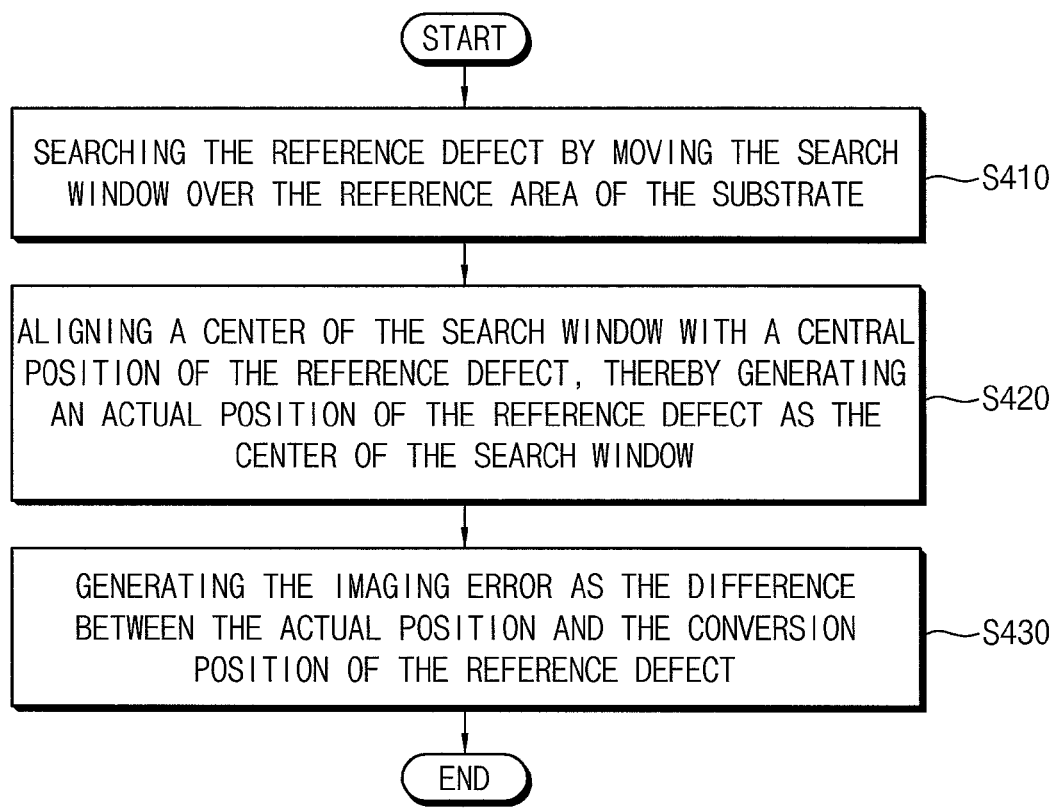
FIG. 7 is a flow chart showing the process step for generating the imaging error shown in FIG. 6.

FIG. 7 is a flow chart showing the process step for generating the imaging error shown in FIG. 6 in accordance with an example embodiment of the present inventive concepts.

Referring to FIG. 7, when the conversion unit 210 completes the coordinate conversion of the inspection positions of the defect D, the search unit 220 may move the search window SW to the reference area of the substrate and may search the reference defect RD (step S410).

The search window SW may search the substrate W with a desired (or alternatively, preset) search size. For example, the search unit 220 may control the size of the search window SW by changing the magnification of the object lens in view of the reference defect size. In the present example embodiment, the reference defect RD may have a defect size of a few hundreds of nanometers and the search window SW may be controlled to have a square size of about 3 µm×3 µm to about 5 µm×5 µm.

In the present example embodiment, the search unit 220 may move the object lens having the search window SW to the reference area of the substrate W, thereby easily and rapidly finding the reference defect RD on the substrate W. Because the reference area of the substrate W is defined (or alternatively, predetermined) before performing the unit process, the position of the reference area may be given to the inspection apparatus 1200 and/or the defect imaging apparatus 1300, the search unit 220 may swiftly move the search window SW to the reference area of the substrate W, thereby facilitating the automatic detection of the reference defect RD on the substrate W.

In the case that the search window SW has the FOV larger than an allowable imaging error range of the image defect apparatus 1300, the search unit 220 may move the search window SW over the reference defect RD with reference to the conversion position, not with reference to the reference area of the substrate W. Supposing that the reference defect RD has a sufficiently large size and the FOV of the search window SW exceeds the allowable imaging error range of the defect imaging apparatus 1300, all of the reference defects RD may be searched for by the search window SW irrespective of the imaging error of the defect imaging apparatus 1300. That is, the search window SW may search for the reference defect RD by using one of the reference area of the substrate W and the conversion position of the reference defect RD.

Then, when the search window SW moves over the reference defect RD, the search unit 220 may align the search window SW with the reference defect RD such that the center SC of the search window SW is in line with the central position of the reference defect RD and then the central position of the search window SW is set up as the actual position of the reference defect RD (step S420).

When the search window SW partially overlaps with the reference defect RD, the search unit 220 may accurately control the search window SW to cover the entire reference defect RD and may detect the overall size and shape of the reference defect RD. Thus, the central position of the reference defect RD may be determined from the overall size and shape of the reference defect RD. Then, the search window SW may move such that the center SC is aligned with the central position of the reference defect RD. When the center SC of the search window SW is in a line with the central position of the reference defect RD in an allowable range, the center SC of the search window SW may be selected as the actual position of the reference defect RD in the defect imaging apparatus 1300.

Then, the actual position and the conversion position of the reference defect RD may be compared with each other and the difference between the actual position and the conversion position may be generated as the imaging error of the defect imaging apparatus 1300 (step S430).

The actual position of the reference defect RD may be transferred to the error generator 230 from the search unit 220 and the conversion position of the reference defect RD may be transferred to the error generator 230 from the first storing section 211.

Because both of the conversion position and the actual position of the reference defect RD may be under the same coordinate system, the imaging error may be calculated as a gap distance between respective coordinate components of the conversion position and the actual position of the reference defect RD.

In the present example embodiment, the Cartesian coordinate system may be used as the defect imaging coordinate system and thus an x-directional gap distance between the x-components and a y-directional gap distance between the y-components may include an x-component and a y-component of the imaging error.

The accuracy of the imaging error may increase as the number of the reference defects RD may increase.

For example, five reference defects RD may be individually searched for from left and right portions, top and bottom portions and a central portion of the substrate W by the search unit 220. Thus, five imaging errors may be generated from each reference defect RD, respectively. Then, a statistical process such as the linear regression may be applied to five equipment errors and a statistically equivalent imaging error (SEIE) of which the statistical deviation from each of the five imaging errors may be minimized. Then, the SEIE may be selected as a single imaging error of the defect imaging apparatus 1300.

The statistical process for obtaining the SEIE may be as follows. An x-component of the SEIE may be obtained by statistically processing five x-components of each imaging error.

First to five actual positions $x1$ to $x5$ may be detected, respectively, by individually aligning the search window SW to each of five reference defects RD, and then first to five x-directional differences $\Delta x1$ to $\Delta x5$ may be obtained by the error generator 230. A regression line may be generated such that a mean value of the deviation between each of the differences $\Delta x1$ to $\Delta x5$ and the regression line may be statistically minimized. In such a case, the regression line may be selected as the SEIE of the defect imaging apparatus 1300.

When an estimated reliability of the regression line is smaller than an allowable reliability of the regression line, a larger number of the reference defects RD may be searched for by the search unit 220 and thus the population size of the x-directional differences may increase. Then, the same statistical process may be carried out to the increased population of the x-directional differences, thereby obtaining an adjusted regression line having an improved reliability. Searching for more reference defects RD to increase a population size for the statistical process and carrying out the statistical process to size-increased differences to thereby generate the adjusted regression line as an improved SEIE may be repeated until an estimated reliability of the adjusted regression line becomes higher than the allowable reliability. In the present example embodiment, the regression line may be expressed as a first order polynomial through a least square method.

A y-component of the statistically equivalent imaging error may be obtained by the same way as described above, Accordingly, the x and y component of the SEIE may include the regression line of which the estimated reliability exceeds the desired (or alternatively, preset) reliability. Such SEIE components may be set up as a single imaging error of the defect imaging apparatus 1300.

For example, the statistical process to a plurality of the differences between the actual points and the conversion positions of a plurality of the reference defects RD may be allowable when the actual positions of a plurality of the reference defects RD may be detected with a sufficient accuracy and in a sufficiently short time. The statistical process to a plurality of the differences may take significant amount of time when the actual positions of the plurality of the reference defects RD are manually detected. Thus, the automatic and accurate detection of the actual positions of the reference defects RD may be desired for the statistical process to a plurality of the differences between the actual points and the conversion positions.

Thereafter, the conversion positions of the process defects PD may be corrected as much as the imaging error by the correction unit 240, thereby generating the irradiation positions of the process defects PD (step S500).

The imaging error may be transferred to the second buffer 242 of the correction unit 240 from the error generator 230 and the conversion positions of the process defects PD may be transferred to the first buffer 241 of the correction unit 240 from the conversion unit 210. The coordinate corrector 243 may individually call the conversion position of each process defect PD and may correct the coordinate value of the conversion position of the process defect PD based on the imaging error by, for example, a linear mapping, and generate the irradiation positions of the process defects PD.

The irradiation position of the process defects PD may be automatically generated by mathematical algorithms such as the linear mapping. Thus, the generation of the conversion position of the defects D, the generation of the imaging error and the correction of the conversion position of the process defects PD may be automatically performed in the defect imaging apparatus 1300. Therefore, the irradiation position of the process defects PD may be automatically and accurately generated in the defect imaging apparatus 1300.

The electron beams E may be irradiated onto the irradiation position on the substrate W, thereby generating the image signal of the process defect PD corresponding to the irradiation position (step S600).

The irradiation position may be transferred to the scan controller 300 and the scan controller 300 may control the beam irradiator 410 and/or the stage 110 in such a way that the electron beams E may be irradiated onto the irradiation position of the substrate W.

Charged particles may be generated from the irradiation position of the substrate W corresponding to the process defect PD in response to the electron beam E and may be detected by the detector 420. The image signal corresponding to the process detect PD may be generated from the detector 420 by processing the charged particles. The image signal may be transferred to the imaging device 500 to generate the defect image of the process defect PD. Therefore, the process defect PD on the substrate W may be accurately and rapidly detected and visualized by the high resolution defect image.

Accordingly, the actual position of the reference defect RD may be automatically obtained in the defect imaging apparatus and the imaging error of the defect imaging apparatus may be accurately obtained. The conversion positions of the process detects PD may be automatically corrected by the imaging error and used as the irradiation positions. Thus, the process defects PD may be automatically and accurately taken into the defect image with higher efficiency.

According to the example embodiments, the defect RD may be intentionally provided on the reference area of the substrate W with a sufficient size for facilitating the automatic detection. The actual position of the reference defect RD obtained by the automatic detection may be compared the conversion position of the same reference defect RD to automatically generate the imaging error of the defect imaging apparatus. Thus, the time and cost for generating the imaging error may be reduced and the accuracy of the imaging error may be increased.

For example, when a plurality of the inspection apparatuses and a plurality of the defect imaging apparatuses are combined in a single defect detection system, the imaging error of the defect imaging apparatus may vary according to the pair of the inspection apparatus and the defect imaging apparatus. In such a case, the automatic detection of the actual positions of a plurality of the reference defects and the automatic generation of the imaging error of each pair of the apparatus may significantly reduce the time and cost no matter how many pairs of the inspection apparatus and the defect imaging apparatus may be provided in the defect detection system.

Further, the automatic detection of the actual positions of the reference defect and the automatic generation of the imaging error may facilitate the statistical treatment of a plurality of differences between a plurality of actual positions and a plurality of conversion positions of a plurality of the reference defects, thereby rapidly generating a more accurate imaging error.

While the present example embodiments disclose apparatuses and/or methods for automatically and accurately detecting defects and generating the defect image of the process defects on the semiconductor substrate, to which the unit manufacturing process for semiconductor devices has been completed. Such apparatuses and/or methods may also be applied to any other substrates as long as pattern structures are formed on the substrate and the process defects of the pattern structure are detected and taken into the defect image. For example, the defect detection and making the defect image of the process defects may also be applied in a unit process of the manufacturing process for flat panel display devices. The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concepts. Accordingly, all such modifications are intended to be included within the scope of the present inventive concepts as defined in the claims. In the claims, means-plus-function clauses are intended to cover the structures described herein as performing the recited functions and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A defect imaging apparatus comprising:
   a chamber having a stage to which a substrate is secured, the substrate having at least one process defect and at least one reference defect defined at a given area;
   a position controller configured to obtain an imaging error from a detected actual position and a conversion position of the reference defect, the position controller further configured to correct a conversion position of the process defect by the imaging error and generate an irradiation position corresponding to an actual location of the process defect;
   an image signal generator configured to generate an image signal of the process defect by irradiating an electron beam to the irradiation position and detecting charged particles discharged from the irradiation position in response to the irradiated electron beam; and
   an imaging device configured to generate a defect image of the process defect by processing the generated image signal.

2. The defect imaging apparatus of claim 1, wherein the position controller includes:
   a conversion unit configured to convert inspection positions of the reference defect and the process defect, which are detected by an inspection apparatus on a basis of an inspection coordinate system, to conversion positions thereof on a basis of an imaging coordinate system;
   a search unit configured to search the reference defect on the substrate and detect an actual position of the reference defect on a basis of the imaging coordinate system;

an error generator configured to generate a difference between the actual position and the conversion position of the reference defect as the imaging error; and a correction unit configured to correct the conversion position of the process defect based on the imaging error and generate the irradiation position based on the corrected conversion position.

3. The defect imaging apparatus of claim 2, wherein the reference defect has a size of about 100 nm to about 900 nm and the search unit is configured to search the reference defect by a unit of a square-shaped field of view having a size of about 3 µm×3 µm to about 5 µm×5 µm.

4. The defect imaging apparatus of claim 2, wherein when the at least one reference defect includes a plurality of reference defects, the error generator is configured to generate a plurality of differences between a plurality of actual positions and a plurality of conversion positions with respect to the reference defects, the plurality of differences including the difference, and the error generator is further configured to generate a statistical equivalent imaging error (SEIE) as the imaging error, the SEIE being a value at which a mean value of deviation between each of the plurality of differences is statistically minimized.

5. The defect imaging apparatus of claim 4, wherein
the imaging coordinate system includes a Cartesian coordinate system, and
x and y components of the statistical equivalent imaging error are determined by a regression line that is expressed into a first order polynomial by a least square method.

6. The defect imaging apparatus of claim 2, wherein
the correction unit includes a first buffer, a second buffer, and a coordinate corrector,
the first buffer is configured to receive the conversion positions of the process defect from the conversion unit,
the second buffer is configured to receive the imaging error from the error generator, and
the coordinate corrector is configured to correct a coordinate value of the conversion position of the process defect based on the imaging error and generate the irradiation position.

7. The defect imaging apparatus of claim 1, further comprising:
a scan controller connected to the position controller, the scan controller configured to control at least one of the image signal generator and the stage such that the electron beam is focused to the irradiation position.

8. The defect imaging apparatus of claim 7, wherein the scan controller includes:
an irradiator controller configured to control a beam irradiator such that a beam path of the electron beam generated by the beam irradiator is directed to the irradiation position; and
a stage controller configured to control the stage such that the irradiation position is aligned with the beam irradiator and the electron beam generated by the beam irradiator is directed to the irradiation position.

9. A method of detecting defects of a substrate, the defects having a plurality of process defects and at least one reference defect defined at a reference area, the method comprising:

performing, by an inspection apparatus, an inspection process to the substrate to generate inspection positions of the defects on a basis of an inspection coordinate system;

transferring the substrate onto a stage of a defect imaging apparatus, the defect imaging apparatus supporting an imaging coordinate system;

converting, by the defect imaging apparatus, the inspection positions of the defects in the inspection coordinate system to conversion positions of the defects in the imaging coordinate system;

generating an imaging error based on a difference between a detected actual position and a conversion position of the reference defect;

correcting the conversion positions of the process defects, respectively, by the imaging error, to generate irradiation positions corresponding to actual positions of the process defects; and generating image signals of the process defects by irradiating an electron beam to the irradiation positions on the substrate.

10. The method of claim 9, wherein the performing an inspection process includes using an optical beam having a wavelength larger than that of the electron beam.

11. The method of claim 9, wherein the generating an imaging error includes:
searching for the reference defect on the substrate by moving a search window over the reference defect;
aligning a center of the search window with a central position of the reference defect;
selecting the center of the search window as the actual position of the reference defect; and
obtaining the difference between the actual position and the conversion position by comparing the actual position and the conversion position of the reference defect.

12. The method of claim 11, wherein when a size of a field of view of a search view is greater than an allowable imaging error range, the search window moves over the reference defect with reference to the conversion position of the reference defect.

13. The method of claim 11, wherein when a size of a field of view of a search view is smaller than an allowable imaging error range, the search window moves over the reference defect with reference to a reference area of the reference defect.

14. The method of claim 11, wherein when the at least one reference defect includes a plurality of reference defects, the generating an imaging error further includes,
performing a statistical process on a plurality of the differences between actual positions and conversion positions of some of the reference defects, and
generating a statistically equivalent imaging error (SEIE) as the image error, the SEIE being a value at which a mean value of deviation from each of the differences is statistically minimized.

15. The method of claim 14, further comprising:
searching for more reference defects to increase a population size for the statistical process, wherein the performing a statistical process includes repeatedly performing the statistical process on size-increased differences to generate an improved SEIE until an estimated reliability of the improved SEIE exceeds a threshold reliability value.

16. A defect imaging apparatus comprising:
a memory having computer-readable instructions stored therein; and at least one processor configured to execute the computer-readable instructions to,
   receive inspection positions of defects on a substrate detected by an inspection apparatus, the defects including a plurality of random process defects and at least one reference defect defined at a reference area, the inspection positions being on a basis of a first coordinate system,
   convert the inspection positions of the defects in the first coordinate system to conversion positions of the defects in a second coordinate system, the second coordinate system being supported by the defect imaging apparatus,
   generate an imaging error based on a difference between an detected actual position and a conversion position of the reference defect,
   correct the conversion positions of the random process defects, respectively, based on the imaging error, to generate irradiation positions corresponding to actual locations of the random process defects, and
   generate image signals of the random process defects by irradiating an electron beam to each of the irradiation positions on the substrate.

17. The defect imaging apparatus of claim 16, wherein the processor is configured to execute the computer-readable instructions to generate the imaging error by,
   searching the reference defect on the substrate by moving a search window over the reference defect,
   aligning a center of the search window with a central position of the reference defect,
   selecting the center of the search window as the actual position of the reference defect, and
   obtaining the difference between the actual position and the conversion position by comparing the actual position and the conversion position of the reference defect.

18. The defect imaging apparatus of claim 16, wherein when the at least one reference defect includes a plurality of reference defects, the processor is configured to execute the computer-readable instructions to generate the imaging error by further,
   performing a statistical process on a plurality of the differences between actual positions and conversion positions of some of the reference defects, and
   generating a statistically equivalent imaging error (SEIE) as the image error, the SEIE being a value at which a mean value of deviation from each of the differences is statistically minimized.

19. The defect imaging apparatus of claim 18, wherein the processor is further configured to execute the computer-readable instructions to generate an improved SEIE by repeatedly performing the statistical process with respect to more of the reference defects until an estimated reliability of the improved SEIE exceeds a threshold reliability value.

20. The defect imaging apparatus of claim 16, wherein the processor is further configured to execute the computer-readable instructions to control at least one of an image signal generator or a stage such that an electron beam irradiated by the image signal generator is focused to the irradiation positions.

* * * * *